United States Patent
Bromidge et al.

(12)

(10) Patent No.: US 6,849,644 B2
(45) Date of Patent: Feb. 1, 2005

(54) ISOQUINOLINE DERIVATIVES USEFUL IN THE TREATMENT OF CNS DISORDERS

(75) Inventors: Steven Mark Bromidge, Harlow (GB); Stephen Frederick Moss, Harlow (GB)

(73) Assignee: SmithKline Beecham p.l.c., Brentford (GB)

(*) Notice: Subject to any disclaimer, the term of this patent is extended or adjusted under 35 U.S.C. 154(b) by 15 days.

(21) Appl. No.: 10/432,446

(22) PCT Filed: Nov. 16, 2001

(86) PCT No.: PCT/EP01/13410

§ 371 (c)(1),
(2), (4) Date: Oct. 3, 2003

(87) PCT Pub. No.: WO02/42293

PCT Pub. Date: May 30, 2002

(65) Prior Publication Data

US 2004/0053956 A1 Mar. 18, 2004

(30) Foreign Application Priority Data

Nov. 21, 2000 (GB) .............................................. 0028380
May 8, 2001 (GB) .............................................. 0111185

(51) Int. Cl.$^7$ ....................... A61K 31/47; C07D 401/12

(52) U.S. Cl. ...................... 514/307; 514/294; 514/300; 546/79; 546/101; 546/113; 546/146; 546/148

(58) Field of Search ........................... 546/79, 101, 113, 546/146, 148; 514/294, 300, 307

(56) References Cited

FOREIGN PATENT DOCUMENTS

| GB | 2 341 549 | 3/2000 |
|---|---|---|
| WO | WO 98 27081 | 6/1998 |
| WO | WO 99 02502 | 1/1999 |

Primary Examiner—Bernard Dentz
(74) Attorney, Agent, or Firm—DSoma G. Simon; Mary E. McCarthy; Charles M. Kinzig

(57) ABSTRACT

The invention relates to novel tetrahydroquinoline compounds having pharmacological activity, processes for their preparation, to compositions containing them and to their use in the treatment of various CNS disorders.

11 Claims, No Drawings

ISOQUINOLINE DERIVATIVES USEFUL IN THE TREATMENT OF CNS DISORDERS

CROSS REFERENCES TO RELATED APPLICATIONS

This application is a National Stage Application filed under 35 U.S.C. §371 of PCT/EP01/13410, filed on Nov. 16, 2001, which claims priority of GB Application No. GB 0028380.4, filed Nov. 21, 2000 and GB Application No. GB 0111185.5, filed May 8, 2001.

This invention relates to novel compounds having pharmacological activity, processes for their preparation, to compositions containing them and to their use in the treatment of CNS and other disorders.

WO 98/27081 discloses a series of aryl sulphonamide compounds that are said to be 5-$HT_6$ receptor antagonists and which are claimed to be useful in the treatment of various CNS disorders. WO 99/47516 and WO 99/65906 both disclose a series of indole derivatives that are claimed to possess 5-$HT_6$ receptor affinity. WO 99/28313 (Merck & Co Inc) describe the preparation of imidazolylmethyltetrahydroisoquinolines and related compounds as inhibitors of farnesyl-protein transferase which are useful in the treatment of cancer, neurofibromin benign proliferative disorder, blindness, hepatitis delta and related viral infections, restenosis and polycystic kidney disease.

A structurally novel class of compounds has now been found which also possess 5-$HT_6$ receptor affinity. The present invention therefore provides, in a first aspect, a compound of formula (I) or a pharmaceutically acceptable salt thereof:

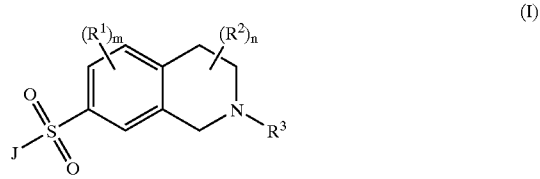

wherein
$R^1$ is halogen, $C_{1-6}$alkyl, $C_{1-6}$alkoxy, $C_{1-6}$alkanoyl, CN, $CF_3$ or $OCF_3$;
$R^2$ is $C_{1-6}$alkyl or a $R^2$ group together with $R^3$ forms a 5 or 6 membered saturated carbocyclic ring;
$R^3$ is hydrogen or a $C_{1-10}$alkyl group optionally substituted by one, two or three substituents selected from the group consisting of halogen, $C_{1-6}$alkoxy, CN, amino, mono- or di-$C_{1-6}$alkylamino or a group —C(O)$OR^7$ where $R^7$ is hydrogen or $C_{1-6}$ alkyl or $R^3$ together with a group $R^2$ forms a 5 or 6 membered saturated carbocyclic ring;
m is 0–3;
n is 0–6;
J is selected from a group of formula (a), (b) or (c) in which:
(a) is a group

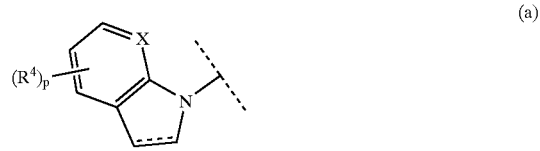

wherein $R^4$ is halogen, $C_{1-6}$alkyl, $C_{1-6}$alkoxy, $C_{1-6}$alkanoyl, $C_{1-6}$alkylthio, hydroxy, CN, $CF_3$, $NO_2$, $OCF_3$, phenyl optionally substituted by groups as defined for $R^1$ above, benzyl, phenyloxy, benzyloxy or $C_{3-6}$cycloalkyloxy or a group $(CH_2)_q NR^8R^9$ where q is 0, 1 or 2 and $R^8$ and $R^9$ are independently hydrogen or $C_{1-6}$alkyl;
p is 0, 1, 2, 3 or 4;
X is CH or N; and ═══ is a single or double bond;
(b) is a group

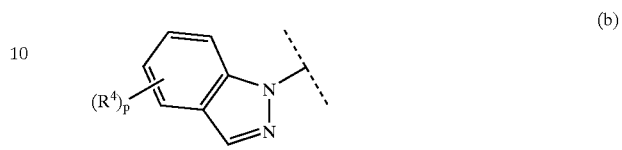

in which $R^4$ and p are as defined for group (a) above; and
(c) is a group

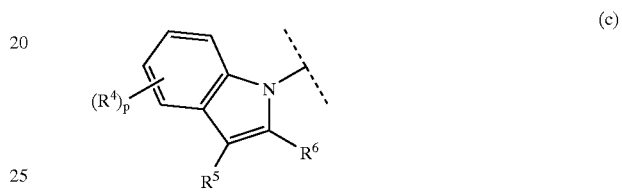

in which $R^4$ and p are as defined for group (a) above and $R^5$ and $R^6$ combine together to form a 5- to 7-membered carbocyclic or heterocyclic ring optionally substituted by groups as defined for $R^1$ above.

Alkyl groups, whether alone or as part of another group, may be straight chain or branched. The term 'halogen' is used herein to describe, unless otherwise stated, a group selected from fluorine, chlorine, bromine or iodine.

When present (i.e. when m is other than 0), the group(s) $R^1$ may be substituted at any suitable carbon atom within the benzene ring. When m is 2 or 3 the groups $R^1$ may be the same or different. Preferred $R^1$ groups are halogen (particularly fluorine, chlorine or bromine) or a $C_{1-6}$alkyl group (particularly methyl). Preferably m is 0 or 1, most preferably 0.

When present (i.e. when n is other than 0), the group(s) $R^2$ may be substituted at any suitable carbon atom within the nitrogen-containing ring. When n is two or more the groups $R^2$ may be same or different. A particularly preferred $R^2$ group is methyl. Preferably, n is 0, 1 or 2. Most preferably, n is 0.

Preferably $R^3$ is hydrogen, methyl or ethyl. Most preferably $R^3$ is hydrogen.

Preferably, J is a group of formula (a) or (c), most preferably (a).

Within the Definition of J Formula (a)

The groups $R^4$ can be substituted at any suitable carbon atom within the bicyclic ring. When p is other than 0, $R^4$ is preferably halogen (particularly fluorine, chlorine or bromine), a $C_{1-6}$alkyl group (particularly methyl), a $C_{1-6}$alkoxy group (particularly methoxy), benzyl, optionally substituted phenyl or a group $(CH_2)_q NR^8R^9$ (particularly $CH_2NMe_2$). Alternatively and preferably, $R^4$ is $CF_3$ or $C_{1-6}$ alkanoyl (particularly $CH_2COOButyl$). When p is 2, 3 or 4 the groups $R^4$ may be the same or different.

Preferably, p is 0, 1 or 2, most preferably p is 1.

Preferably ═══ is a double bond.

Preferably X is CH.

When X is CH and === is a double bond, most preferably R⁴ represents optionally substituted phenyl attached at the C-3 of the bicyclic ring, especially unsubstituted phenyl.
Within the Definition of J Formula (b)
The groups R⁴ can be substituted at any suitable carbon atom in the indazole ring. Preferred R⁴ groups include those given for formula (a) above.
Preferably, p is 1.
Preferably, R⁴ represents halogen, particularly chlorine.
Within the Definition of J Formula (c)
The groups R⁴ can be substituted at any suitable carbon atom. Preferred R⁴ groups include those given for formula (a) above.
The 5- to 7-membered heterocyclic ring formed by the combination of groups R⁵ and R⁶ may be saturated, unsaturated or partially saturated. Preferably R⁵ and R⁶ combine together to form a 6 membered carbocyclic or heterocyclic ring. Most preferably, R⁵ and R⁶ combine such that the group J is a carbazole or tetrahydrocarbazole ring.
Preferably, p is 0.
In one aspect of the present invention we provide a compound of formula (IB) or a pharmaceutically acceptable salt thereof:

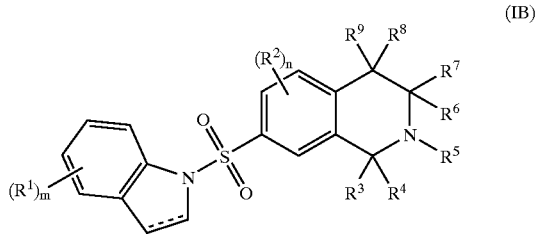

(IB)

wherein:
R¹, is halogen, $C_{1-6}$alkyl, $C_{1-6}$alkoxy, $C_{1-6}$alkanoyl, CN, $CF_3$, $OCF_3$, phenyloxy, benzyloxy or $C_{3-6}$cycloalkyloxy;
m' is 0–4;
R²' is as defined for R¹' above;
n' is 0–3;
R³', R⁴' R⁶', R⁷', R⁸' and R⁹' are independently hydrogen or $C_{1-6}$alkyl or R⁴', together with the group R⁵', forms a 5 or 6 membered saturated ring;
R⁵' is hydrogen, a $C_{1-10}$alkyl group optionally substituted by one, two or three substituents selected from the group consisting of halogen, $C_{1-6}$alkoxy, CN, amino, mono- or di-$C_{1-6}$alkylamino or a group —C(O)OR¹⁰' where R¹⁰' is hydrogen or $C_{1-6}$ alkyl or R⁵' together with group R⁴' forms a 5 or 6 membered saturated ring; === is a single or double bond.

Particularly preferred compounds according to the invention include examples 1–35 (as shown below) or a pharmaceutically acceptable salt thereof.

A more particularly preferred compound of formula (I) includes 7-(3-Phenyl-indole-1-sulfonyl)-1,2,3,4-tetrahydroisoquinolie hydrochloride (E35) or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic, trifluoroacetic or naphthalenesulfonic acid.

The compounds of formula (I) may be prepared in crystalline or non-crystalline form, and, if crystalline, may optionally be hydrated or solvated. This invention includes within its scope stoichiometric solvates eg. hydrates as well as compounds containing variable amounts of solvent eg. water.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

In a further aspect, the present invention also provides a process for the preparation of a compound of formula (I) or a pharmaceutically acceptable salt thereof, which process comprises the coupling of a compound of formula (II):

J-H                                                        (II)

in which J is as defined in formula (I) with a compound of formula (III) or a protected derivative thereof;

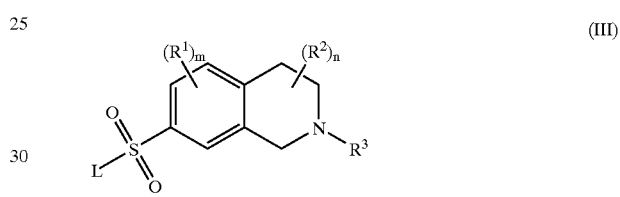

(III)

in which R¹–R³, m and n are as defined in formula (I) and L is a leaving group and optionally thereafter:
 converting a compound of formula (I) into another compound of formula (I);
 removing any protecting groups;
 forming a pharmaceutically acceptable salt.

Suitable leaving groups include halogen, in particular chloro. The reaction of compounds of formulae (II) and (III) may be carried out by mixing the two reagents together, optionally under phase-transfer conditions, in a mixture of an inert organic solvent such as tetrahydrofuran with an aqueous base such as sodium hydroxide with the addition of a suitable phase-transfer catalyst such as tetrabutylammonium hydroxide. Alternatively, the reaction of compounds of formulae (II) and (III) may be carried out by treating a compound of formula (II) with a suitable base such as sodium hydride or sodium hexamethyldisilazane (NaHMDS) in an inert solvent such as tetrahydrofuran or N,N-dimethylformamide to form the anion of (II) and then treating this with a compound of formula (III) in an inert solvent. For compounds of formula (I) in which J is a group of formula (a) and === is a single bond, the reaction of compounds of formulae (II) and (III) may be carried out by mixing the two reagents together, optionally in an inert solvent such as dichloromethane with or without the addition of a suitable base such as triethylamine or pyridine.

Where R³ is hydrogen, suitable protecting groups for the resulting free NH include carbonyl-containing protecting groups e.g. acetyl, trifluoroacetyl or 2,2,2-trichloroethoxycarbonyl.

Compounds of formula (I) can be converted into further compounds of formula (I) using standard techniques. The following example is given by way of illustration. For compounds of formula (I) wherein R³ is hydrogen, it is possible to introduce an alternative R³ group by conventional alkylation using 1 molar equivalent of an alkylhalide and 1 molar equivalent of a suitable base in an inert solvent.

It will be appreciated by those skilled in the art that it may be necessary to protect certain reactive substituents during some of the above procedures. Standard protection and deprotection techniques, such as those described in Greene T. W. 'Protective groups in organic synthesis', New York, Wiley (1981), can be used. For example, primary amines can be protected as acyl (eg. acetyl), phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art.

Compounds of formulae (II) and (III) are commercially available, may be prepared using procedures described herein or by analogous methods thereto or according to known methods.

Pharmaceutically acceptable salts may be prepared conventionally by reaction with the appropriate acid or acid derivative.

Compounds of formula (I) and their pharmaceutically acceptable salts have 5-HT$_6$ receptor activity and are believed to be of potential use in the treatment of certain CNS disorders such as anxiety, depression, epilepsy, obsessive compulsive disorders, migraine, cognitive memory disorders e.g. Alzheimers disease and age related cognitive decline, Parkinsons Disease, ADHD (Attention Deficit Disorder/Hyperactivity Syndrome), sleep disorders (including disturbances of Circadian rhythm), feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI (gastrointestinal) disorders such as IBS (Irritable Bowel Syndrome). Compounds of the invention are further expected to be of use in the treatment of mild cognitive impairment.

Thus the invention also provides a compound of formula (I) or a pharmaceutically acceptable salt thereof, for use as a therapeutic substance, in particular in the treatment or prophylaxis of the above disorders. In particular the invention provides for a compound of formula (I) or a pharmaceutically acceptable salt thereof, for use in the treatment of depression, anxiety, Alzheimers disease, age related cognitive decline and ADHD. Also in particular the invention provides for a compound of formula (I) or a pharmaceutically acceptable salt thereof, for use in the treatment of mild cognitive impairment and schizophrenia.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment or prophylaxis of the above disorders.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three times a day, so that the total daily dosage is in the range of about 0.5 to 100 mg; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

DESCRIPTION 1

1-[7-(Indole-1-sulfonyl)-3,4-dihydro-1H-isoquinolin-2-yl]-ethanone (D1)

A 50% solution of sodium hydroxide (100 ml) was added to a vigorously stirred solution of indole (5.8 g, 50 mmol)

and tetrabutylammonium hydroxide (40% by weight solution, 2 ml, 3.1 mmol) in tetrahydrofuran (100 ml). After 5 minutes, a solution of 2-acetyl-1,2,3,4-tetrahydroisoquinoline-7-sulfonyl chloride (R. G. Pendleton et al., *J. Pharmacol. Exp. Ther.*, 1979, 208, 24; U.S. Pat. No. 3,725,388 (1973)) (13.7 g, 50 mmol) in tetrahydrofuran (50 ml) was added over 10 minutes and the resulting mixture was vigorously stirred for a further 3 h. The mixture was then extracted with ethyl acetate (250 ml) and the extract dried ($MgSO_4$), concentrated in vacuo and the residue purified by column chromatography over silica gel eluting with a dichloromethane/methanol gradient to give the title compound (D1) (12.8 g, 72%), NMR ($CDCl_3$; rotamers observed)/ppm 2.12, 2.14 (3H, 2xs), 2.77–2.88 (2H, m), 3.60, 3.74 (3H, 2xt J=7 Hz), 4.59, 4.68 (2H, 2xs), 6.65–6.67 (1H, m), 7.16–7.34 (3H, m), 7.50–7.69 (4H, m), 7.94–7.99 (1H, m); MS: m/z ($MH^+$) 355.

DESCRIPTION 2

1-(4,4-Dimethyl-3,4-dihydro-1H-isoquinolin-2-yl)-ethanone (D2)

A solution of acetic anhydride (1.17 ml, 12.4 mmol) was added dropwise to a stirred, ice-cooled solution of 4,4-dimethyl-1,2,3,4-tetrahydro-isoquinoline (1.0 g, 6.2 mmol) (for preparation see *J. Org. Chem.*, 1983, 48, 5348) in dry dichloromethane (5 ml). The cooling bath was removed and the solution was stirred for 2 h at room temperature. The reaction mixture was then concentrated in vacuo to give the title compound (D2) as an oil (1.1 g, 87%), δH ($CDCl_3$, rotamers observed)/ppm 1.28, 1.32 (6H, 2xs), 2.20, 2.22 (3H, 2xs), 3.43, 3.61 (2H, 2xs), 4.66, 4.77 (2H, 2xs), 7.07–7.37 (4H, m).

DESCRIPTION 3

2-Acetyl-4,4-dimethyl-1,2,3,4-tetrahydro-isoquinoline-7-sulfonyl Chloride (D3)

A solution of 1-(4,4-dimethyl-3,4-dihydro-1H-isoquinolin-2-yl)-ethanone (D2) (0.5 g, 2.5 mmol) in dry dichloromethane (2 ml) was added over 15 minutes to an ice-cooled, stirred solution of chlorosulfonic acid (1.7 ml, 25 mmol) in dry dichloromethane (6 ml). After stirring the solution at 0° C. for 1 h, it was warmed to ambient temperature and stirred for a further 3 h. The solution was then carefully poured onto a mixture of ice (30 g) and water (30 ml) with stirring. The layers were separated and the aqueous layer was extracted with dichloromethane (30 ml). The combined organic layers were dried ($MgSO_4$) and concentrated in vacuo to an oil which was stirred at room temperature for 15 minutes with diethyl ether (30 ml) to afford the title compound (D3) as a white solid (0.21 g, 27%), δH ($CDCl_3$, rotamers observed)/ppm 1.33, 1.37 (6H, 2xs), 2.21, 2.24 (3H, 2xs), 3.47, 3.66 (2H, 2xs), 4.77, 4.88 (2H, 2xs), 7.55–7.62 (1H, m), 7.77–7.90 (2H, m).

DESCRIPTION 4

1-[7-(6-Chloro-indole-1-sulfonyl)-4,4-dimethyl-3,4-dihydro-1H-isoquinolin-2-yl]-ethanone (D4)

Potassium tert-butoxide (37 mg, 0.33 mmol) was added to a stirred solution of 6-chloroindole (50 mg, 0.33 mmol) in dry tetrahydrofuran (1 ml) under argon at room temperature. After stirring for 5 minutes, a solution of 2-acetyl-4,4-dimethyl-1,2,3,4-tetrahydro-isoquinoline-7-sulfonyl chloride (D3) (100 mg, 0.33 mmol) in dry tetrahydrofuran (1 ml) was added and the solution was stirred for a further 3 h. Ethyl acetate (5 ml) and water (5 ml) were added to the reaction mixture, which was then shaken. The layers were separated and the organic phase was washed with brine (5 ml), dried ($MgSO_4$) and concentrated in vacuo to an oil. The oil was purified by column chromatography over silica gel eluting with a gradient of acetone/toluene to afford the title compound (D4) (70 mg, 51%), MS: m/z ($MH^+$) 417/419.

DESCRIPTION 5

1-[7-(2,3-Dihydro-indole-1-sulfonyl)-3,4-dihydro-1H-isoquinolin-2-yl]-ethanone (D5)

Pyridine (0.85 ml, 10.5 mmol) was added to a stirred solution of 2-acetyl-1,2,3,4-tetrahydroisoquinoline-7-sulfonyl chloride (0.96 g, 3.5 mmol) and 2,3-dihydro-1H-indole (0.42 g, 3.5 mmol) in 1,2-dichlorethane (40 ml) at room temperature. After 3 h, the solution was washed with water (40 ml), dried (MgSO4) and concentrated in vacuo to an oil. The oil was purified by column chromatography over silica gel eluting with a gradient of dichloromethane/methanol to afford the title compound (D5) as an oil (0.83 g, 67%), MS: m/z ($MH^+$) 357.

DESCRIPTION 6

3,4-Dihydro-1H-isoquinoline-2-carboxylic Acid 2,2,2-Trichloro-ethyl Ester (D6)

Tetrahydroisoquinoline [Aldrich] (39.9 g, 300 mmol) was dissolved in dichloromethane (400 ml) and treated with triethylamine (32 g, 315 mmol). The mixture was cooled in an ice bath and a solution of 2,2,2-trichloroethylchloroformate (65.0 g, 306 mmol) in dichloromethane (100 ml) introduced dropwise over 15 minutes. After addition, the mixture was allowed to warm to room temperature and stirred for a further 30 minutes. The solution was washed with 1M aqueous hydrochloric acid (2×100 ml), then washed successively with water (100 ml), sodium bicarbonate (100 ml) and brine (50 ml), then dried ($MgSO_4$), filtered and evaporated to give the title compound (D6) as a pale orange oil 92.5 g; δH ($CDCl_3$ rotamers observed) ppm 2.90 (2H, app.t), 3.74–3.81 (2H, m), 4.67, 4.72 (2H, 2s), 4.80 (2H, s), 7.12–7.21 (4H, m).

DESCRIPTION 7

7-Chlorosulfonyl-3,4-dihydro-1H-isoquinoline-2-carboxylic Acid 2,2,2-Trichloro-ethyl Ester (D7)

Crude 3,4-dihydro-1H-isoquinoline-2-carboxylic acid 2,2,2-trichloro-ethyl ester (D6) (46 g, 150 mmol) was added dropwise over 40 minutes to chlorosulphonic acid (70 ml) cooled with an ice bath to maintain the temperature between 5 and 15° C. The mixture was then allowed to warm to room temperature, stirred for 16 hours, then poured onto crushed ice (500 ml) and dichloromethane (500 ml) added. This mixture was washed with water (3×250 ml), and brine (50 ml) then dried (sodium sulphate), filtered and evaporated to an orange oil which slowly crystallised on standing. This was recrystallised from ether-hexane to give the title compound (D7) as a white crystalline solid (64.5 g 83%); δH ($CDCl_3$) ppm 3.03 (2H, app.t), 3.81–3.86 (2H, m), 4.74–4.85 (4H, m), 7.42 (1H, d), 7.82–7.88 (2H, m).

EXAMPLE 1

7-(Indole-1-sulfonyl)-1,2,3,4-tetrahydro-isoquinoline Hydrochloride (E1)

A mixture of 1-[7-(indole-1-sulfonyl)-3,4-dihydro-1H-isoquinolin-2-yl]-ethanone (D1) (12 g, 34 mmol) in 3M hydrochloric acid (200 ml) and n-butanol (100 ml) was refluxed for 7 h. The reaction mixture was evaporated in vacuo to dryness and the residue was recrystallized from 2-propanol/diethyl ether to give the title compound (E1) (8.5 g, 72%), NMR (D6-DMSO) 3.03 (2H, t, J=6.0 Hz), 3.29 (2H, t, J=6.0 Hz), 4.29 (2H, s), 6.85 (1H, d, J=3.7 Hz), 7.22–7.43 (3H, m), 7.60 (1H, d, J=7.6 Hz), 7.79–7.85 (2H, m), 7.94–8.01 (2H, m); MS: m/z (MH$^+$) 313.

The following compounds were prepared as hydrochloride or oxalate salts by a sequential two step procedure as described in Description D1, using the appropriate indole or indazole with 2-acetyl-1,2,3,4-tetrahydroisoquinoline-7-sulfonyl chloride, and Example 1, in which N-deacetylation is carried out. An alternative method is described in Descriptions D6 and D7 and exemplified in Example 35 in which 7-chlorosulfonyl-3,4-dihydro-1H-isoquinoline-2-carboxylic acid 2,2,2-trichloro-ethyl ester (D7) is condensed with the appropriate indole prior to removal of the trichloroethyl carbamate group. The final products were purified either by column chromatography eluting with a dichloromethane/methanol gradient, or by trituration of the salt with diethyl ether.

| Compound | MH$^+$ |
|---|---|
| 7-(5-Bromo-indole-1-sulfonyl)-1,2,3,4-tetrahydro-isoquinoline (E2) | 391/393 |
| 7-(5-Chloro-indole-1-sulfonyl)-1,2,3,4-tetrahydro-isoquinoline (E3) | 347/349 |
| Dimethyl-[1-(1,2,3,4-tetrahydro-isoquinoline-7-sulfonyl)-1H-indol-3-ylmethyl]-amine (E4) | 370 |
| 7-(5-Fluoro-indole-1-sulfonyl)-1,2,3,4-tetrahydro-isoquinoline (E5) | 331 |
| 7-(4-Methoxy-indole-1-sulfonyl)-1,2,3,4-tetrahydro-isoquinoline (E6) | 343 |
| 7-(5-Methoxy-indole-1-sulfonyl)-1,2,3,4-tetrahydro-isoquinoline (E7) | 343 |
| 7-(5-Methoxy-2-methyl-indole-1-sulfonyl)-1,2,3,4-tetrahydro-isoquinoline (E8) | 357 |
| 9-(1,2,3,4-Tetrahydro-isoquinoline-7-sulfonyl)-2,3,4,9-tetrahydro-1H-carbazole (E9) | 367 |
| 7-(3-Methyl-indole-1-sulfonyl)-1,2,3,4-tetrahydro-isoquinoline (E10) | 327 |
| 7-(3-Phenyl-indole-1-sulfonyl)-1,2,3,4-tetrahydro-isoquinoline (E11) | 389 |
| 7-(3-Benzyl-indole-1-sulfonyl)-1,2,3,4-tetrahydro-isoquinoline (E12) | 403 |
| 7-(5-Fluoro-2-phenyl-indole-1-sulfonyl)-1,2,3,4-tetrahydro-isoquinoline (E13) | 407 |
| 7-(5-Benzyl-indole-1-sulfonyl)-1,2,3,4-tetrahydro-isoquinoline (E14) | 403 |
| 7-(2,3-Dimethyl-indole-1-sulfonyl)-1,2,3,4-tetrahydro-isoquinoline (E15) | 341 |
| 7-(6-Chloro-indole-1-sulfonyl)-1,2,3,4-tetrahydro-isoquinoline (E16) | 347/349 |
| 7-(4-Chloro-indole-1-sulfonyl)-1,2,3,4-tetrahydro-isoquinoline (E17) | 347/349 |
| 7-(4,6-Difluoro-indole-1-sulfonyl)-1,2,3,4-tetrahydro-isoquinoline (E18) | 349 |
| 7-(6-Methoxy-indole-1-sulfonyl)-1,2,3,4-tetrahydro-isoquinoline (E19) | 343 |
| 7-(6-Methyl-indole-1-sulfonyl)-1,2,3,4-tetrahydro-isoquinoline (E20) | 327 |
| 7-(4-Methyl-indole-1-sulfonyl)-1,2,3,4-tetrahydro-isoquinoline (E21) | 327 |
| 7-(6-Fluoro-indole-1-sulfonyl)-1,2,3,4-tetrahydro-isoquinoline (E22) | 331 |
| 7-(5,6-Difluoro-indole-1-sulfonyl)-1,2,3,4-tetrahydro-isoquinoline (E23) | 349 |
| 7-(6-Trifluoromethyl-indole-1-sulfonyl)-1,2,3,4-tetrahydro-isoquinoline (E24) | 381 |
| [1-(1,2,3,4-tetrahydro-isoquinoline-7-sulfonyl)-1H-indol-3-yl]-acetic acid butyl ester (E25) | 427 |
| 9-(1,2,3,4-tetrahydro-isoquinoline-7-sulfonyl)-9H-carbazole (E26) | 363 |
| 7-(3-Chloro-indazole-1-sulfonyl)-1,2,3,4-tetrahydro-isoquinoline (E27) | 348/350 |

EXAMPLE 28

7-(6-Chloro-indole-1-sulfonyl)-4,4-dimethyl-1,2,3,4-tetrahydro-isoquinoline (E28)

1-[7-(6-Chloro-indole-1-sulfonyl)-4,4-dimethyl-3,4-dihydro-1H-isoquinolin-2-yl]-ethanone (D4) was N-deacetylated as described in Example 1 to afford, after treatment with sodium hydrogen carbonate solution, the title compound (E28). Treatment of a solution of this material in dichloromethane/diethyl ether with oxalic acid (1.5 equivalents) afforded the corresponding crystalline oxalate salt (65 mg, 42%), δH (CD$_3$OD)/ppm 1.13 (6H, s), 2.71 (2H, br,s), 3.86 (2H, br,s), 6.61 (1H, d, J=3.7 Hz), 7.12 (1H, dd, J=8.4, 1.8 Hz), 7.40–7.86 (4H, m), 7.86 (1H, d, J=1.7 Hz). MS: m/z (MH$^{30}$) 375/377.

The following compounds were prepared as oxalate salts by a sequential two step procedure as described in Description D4, using the appropriate indole with 2-acetyl-4,4-dimethyl-1,2,3,4-tetrahydro-isoquinoline-7-sulfonyl chloride (D3), and Example 1, in which N-deacetylation is carried out.

| Compound | MH$^+$ |
|---|---|
| 9-(4,4-Dimethyl-1,2,3,4-tetrahydro-isoquinoline-7-sulfonyl)-2,3,4,9-tetrahydro-1H-carbazole (E29) | 395 |
| [1-(4,4-Dimethyl-1,2,3,4-tetrahydro-isoquinoline-7-sulfonyl)-1H-indol-3-ylmethyl]-dimethyl-amine (E30) | 398 |
| 4,4-Dimethyl-7-(3-methyl-indole-1-sulfonyl)-1,2,3,4-tetrahydro-isoquinoline (E31) | 355 |
| 4,4-Dimethyl-7-(6-trifluoromethyl-indole-1-sulfonyl)-1,2,3,4-tetrahydro-isoquinoline (E32) | 409 |
| 7-(6-Methoxy-indole-1-sulfonyl)-4,4-dimethyl-1,2,3,4-tetrahydro-isoquinoline (E33) | 371 |

EXAMPLE 34

7-(2,3-Dihydro-indole-1-sulfonyl)-1,2,3,4-tetrahydro-isoquinoline (E34)

The title compound (E34) was prepared from 1-[7-(2,3-dihydro-indole-1-sulfonyl)-3,4-dihydro-1H-isoquinolin-2-yl]-ethanone (D5) by the method described in Example 1: MS: m/z (MH$^+$) 315.

EXAMPLE 35

7-(3-Phenyl-indole-1-sulfonyl)-1,2,3,4-tetrahydro-isoquinoline Hydrochloride (E35)

3-Phenylindole [Heterocycl. Commun. (2000), 6(1), 59–62](2 mmol, 390 mg), was added to a stirred suspension of sodium hydride (40% oil dispersion, 88 mg, 2.2 mmol) in tetrahydrofuran (15 ml). When the effervescence ceased, 7-chlorosulfonyl-3,4-dihydro-1H-isoquinoline-2-carboxylic acid 2,2,2-trichloro-ethyl ester (D7) (840 mg, 2 mmol) was added and the mixture stirred at RT for 36 hours. The mixture was treated with saturated aq sodium carbonate (100 ml) and extracted with dichloromethane (3×50 ml). The combined extracts were dried ($MgSO_4$) filtered and evaporated to afford a brown oil which was dissolved in THF (20 ml) and treated with sodium dihydrogen phosphate (10 ml) and zinc dust (1.0 g). The mixture was stirred vigorously for 36 h, filtered, washing the solid with water (10 ml) and THF (10 ml). The filtrate was treated with 10% aqueous potassium carbonate (20 ml) and the mixture extracted with dichloromethane (3×50 ml). The combined organic phase was dried ($MgSO_4$), filtered, evaporated and the residue purified by flash chromatography (methanol-dichloromethane-aqueous ammonia) to afford the free base of the title compound δH ($CHCl_3$)/ppm 2.73–2.79 (2H, m), 3.06 (2H, app.t), 3.94, 3.97 (2H, 2s), 7.03–7.69 (11H, m), 7.78 (1H, d), 8.04 (1H, d), MS[ES]: m/z ($MH^+$) 389. This was converted to the title compound (E35) by treatment with 1M HCl in diethyl ether. $R_f$ silica gel (1% (35% aq. $NH_3$), 9% MeOH, 90% $CHCl_3$) 0.40; $δ_{max}$ ($CHCl_3$) 3422, 2959, 2761, 1604, 1445, 1372, 1166, 1134 cm-1; δH ($CHCl_3$) 1.7 (2H, br.s), 3.09–3.10 (2H, m), 3.28–3.30 (2H, m), 4.24, 4.29 (2H, 2s), 7.19–7.78 (12H, m), 8.04 (1H, d); m.p. (diethyl ether-methanol) (with decomposition) 193–197° C.

Pharmacological Data

Compounds can be tested following the procedures outlined in WO 98/27081.

All examples were found to have a pKi in the range 6.7–8.9 at human cloned 5-$HT_6$ receptors.

Furthermore, Examples E1, E9–E11, E13, E16–17, E19–24, E26 and E35 were found to have a pKi in the range 8.2–8.9.

What is claimed is:

1. A compound of formula (I) or a pharmaceutically acceptable salt thereof:

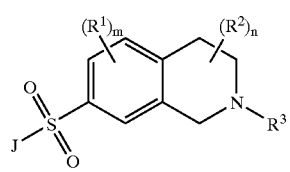

(I)

wherein
 $R^1$ is halogen, $C_{1-6}$alkyl, $C_{1-6}$alkoxy, $C_{1-6}$alkanoyl, CN, $CF_3$ or $OCF_3$;
 $R^2$ is $C_{1-6}$alkyl or a $R^2$ group together with $R^3$ forms a 5 or 6 membered saturated carbocyclic ring;
 $R^3$ is hydrogen or a $C_{1-10}$alkyl group optionally substituted by one, two or three substituents selected from the group consisting of halogen, $C_{1-6}$alkoxy, CN, amino, mono- or di-$C_{1-6}$alkylamino or a group —C(O)$OR^7$ where $R^7$ is hydrogen or $C_{1-6}$alkyl or $R^3$ together with a group $R^2$ forms a 5 or 6 membered saturated carbocyclic ring;

m is 0–3;
n is 0–6;
J is selected from a group of formula (a), (b) or (c) in which:
 (a) is a group

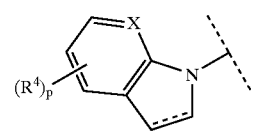

(a)

wherein $R^4$ is halogen, $C_{1-6}$alkyl, $C_{1-6}$alkoxy, $C_{1-6}$alkanoyl, $C_{1-6}$alkylthio, hydroxy, CN, $CF_3$, $NO_2$, $OCF_3$, phenyl optionally substituted by groups as defined for $R^1$ above, benzyl, phenyloxy, benzyloxy or $C_{3-6}$cycloalkyloxy or a group $(CH_2)_q NR^8R^9$ where q is 0, 1 or 2 and $R^8$ and $R^9$ are independently hydrogen or $C_{1-6}$alkyl;
p is 0, 1, 2, 3 or 4;
X is CH or N; and
═══ is a single or double bond;
 (b) is a group

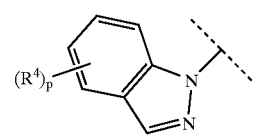

(b)

in which $R^4$ and p are as defined for group (a) above; and
 (c) is a group

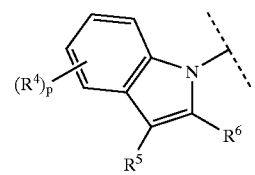

(c)

in which $R^4$ and p are as defined for group (a) above and $R^5$ and $R^6$ combine together to form a 5- to 7- membered carbocyclic or heterocyclic ring optionally substituted by groups as defined for $R^1$ above.

2. A compound according to claim 1 in which J is a group of formula (a) and X is CH.

3. A compound according to claim 1 in which $R^3$ is hydrogen.

4. A compound according to claim 1 in which m is 0.

5. A compound according to claim 1 in which n is 0.

6. A compound according to claim 1 in which $R^4$ represents halogen or optionally substituted phenyl.

7. A compound according to claim 1 which is:
 7-(Indole-1-sulfonyl)-1 2,3,4-tetrahydro-isoquinoline;
 7-(5-Bromo-indole-1-sulfonyl)-1,2,3,4-tetrahydro-isoquinoline;
 7-(5-Chloro-indole-1-sulfonyl)-1,2,3,4-tetrahydro-isoquinoline;
 Dimethyl-[1-(1,2,3,4-tetrahydro-isoquinoline-7-sulfonyl)-1H-indol-3-ylmethyl]-amine;
 7-(5-Fluoro-indole-1-sulfonyl)-1,2,3,4-tetrahydro-isoquinoline;
 7-(4-Methoxy-indole-1-sulfonyl)-1,2,3,4-tetrahydro-isoquinoline;

7-(5-Methoxy-indole-1-sulfonyl)-1,2,3,4-tetrahydro-isoquinoline;
7-(5-Methoxy-2-methyl-indole-1-sulfonyl)-1,2,3,4-tetrahydro-isoquinoline;
9-(1,2,3,4-Tetrahydro-isoquinoline-7-sulfonyl)-2,3,4,9-tetrahydro-1H-carbazole;
7-(3-Methyl-indole-1-sulfonyl)-1,2,3,4-tetrahydro-isoquinoline;
7-(3-Phenyl-indole-1-sulfonyl)-1,2,3,4-tetrahydro-isoquinoline;
7-(3-Benzyl-indole-1-sulfonyl)-1,2,3,4-tetrahydro-isoquinoline;
7-(5-Fluoro-2-phenyl-indole-1-sulfonyl)-1,2,3,4-tetrahydro-isoquinoline;
7-(5-Benzyl-indole-1-sulfonyl)-1,2,3,4-tetrahydro-isoquinoline;
7-(2,3-Dimethyl-indole-1-sulfonyl)-1,2,3,4-tetrahydro-isoquinoline;
7-(6-Chloro-indole-1-sulfonyl)-1,2,3,4-tetrahydro-isoquinoline;
7-(4-Chloro-indole-1-sulfonyl)-1,2,3,4-tetrahydro-isoquinoline;
7-(4,6-Difluoro-indole-1-sulfonyl)-1,2,3,4-tetrahydro-isoquinoline;
7-(6-Methoxy-indole-1-sulfonyl)-1,2,3,4-tetrahydro-isoquinoline;
7-(6-Methyl-indole-1-sulfonyl)-1,2,3,4-tetrahydro-isoquinoline;
7-(4-Methyl-indole-1-sulfonyl)-1,2,3,4-tetrahydro-isoquinoline;
7-(6-Fluoro-indole-1-sulfonyl)-1,2,3,4-tetrahydro-isoquinoline;
7-(5,6-Difluoro-indole-1-sulfonyl)-1,2,3,4-tetrahydro-isoquinoline;
7-(6-Trifluoromethyl-indole-1-sulfonyl)-1,2,3,4-tetrahydro-isoquinoline;
[1-(1,2,3,4-tetrahydro-isoquinoline-7-sulfonyl)-1H-indol-3-yl]-acetic acid butyl ester;
9-(1,2,3,4-tetrahydro-isoquinoline-7-sulfonyl)-9H-carbazole;
7-(3-Chloro-indazole-1-sulfonyl)-1,2,3,4-tetrahydro-isoquinoline;
7-(6-Chloro-indole-1-sulfonyl)-4,4-dimethyl-1,2,3,4-tetrahydro-isoquinoline;
9-(4,4-Dimethyl-1,2,3,4-tetrahydro-isoquinline-7-sulfonyl)-2,3,4,9-tetrahydro-1H-carbazole;
[1-(4,4-Dimethyl-1,2,3,4-tetrahydro-isoquinoline-7-sulfonyl)-1H-indol-3-ylmethyl]-dimethyl-amine;
4,4-Dimethyl-7-(3-methyl-indole-1-sulfonyl)-1,2,3,4-tetrahydro-isoquinoline;
4,4-Dimethyl-7-(6-trifluoromethyl-indole-1-sulfonyl)-1,2,3,4-tetrahydro-isoquinoline;
7-(6-Methoxy-indole-1-sulfonyl)-4,4-dimethyl-1,2,3,4-tetrahydro-isoquinoline;
7-(2,3-Dihydro-indole-1-sulfonyl)-1,2,3,4-tetrahydro-isoquinoline;
7-(3-Phenyl-indole-1-sulfonyl)-1,2,3,4-tetrahydro-isoquinoline;
or a pharmaceutically acceptable salt thereof.

8. A method of treatment of depression, anxiety, Alzheimers disease, age related cognitive decline, Attention Deficit Disorder/Hyperactivity Syndrome, mild cognitive impairment and/or schizophrenia which comprises administering to a patient an effective amount of a compound of formula (I) as defined in claim 1.

9. A pharmaceutical composition comprising a therapeutically effective amount of a compound of formula (I) as defined in claim 1 for use in treatment of depression, anxiety, Alzheimers disease, age related cognitive decline, Attention Deficit Disorder/Hyperactivity Syndrome, mild cognitive impairment and/or schizophrenia.

10. A process for the preparation of a compound of formula (I) or a pharmaceutically acceptable salt thereof, which process comprises the coupling of a compound of formula (II):

J-H  (II)

in which J is as defined in formula (I) with a compound of formula (III) or a protected derivative thereof;

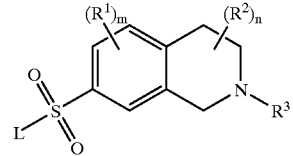

(III)

in which $R^1$–$R^3$, m and n are as defined in formula (I) and L is a leaving group and optionally thereafter:
 converting a compound of formula (I) into another compound of formula (I);
 removing any protecting groups;
 forming a pharmaceutically acceptable salt.

11. A pharmaceutical composition which comprises a therapeutically effective amount of a compound according to claim 1 and a pharmaceutically acceptable carrier or excipient.

* * * * *